United States Patent
Lin et al.

(10) Patent No.: US 6,221,979 B1
(45) Date of Patent: Apr. 24, 2001

(54) MIXTURES OF SILICONE ELASTOMERS

(75) Inventors: Zuchen Lin; William James Schulz, Jr., both of Midland; Janet Mary Smith, Bay City, all of MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/435,044

(22) Filed: Nov. 8, 1999

(51) Int. Cl.[7] ............................................... C08G 77/46
(52) U.S. Cl. ........................... 525/477; 524/588; 528/15; 516/23; 516/903; 516/906
(58) Field of Search .................... 525/477; 524/588; 516/23, 903, 906; 528/15

(56) References Cited

U.S. PATENT DOCUMENTS

| | | | |
|---|---|---|---|
| 4,698,178 | * 10/1987 | Huttunger et al. | |
| 5,811,487 | 9/1998 | Schulz | 524/862 |
| 5,880,210 | 3/1999 | Schulz | 524/731 |
| 5,948,855 | 9/1999 | Lin | 524/837 |

FOREIGN PATENT DOCUMENTS

02903247 * 6/1999 (JP) .

* cited by examiner

Primary Examiner—Robert Dawson
Assistant Examiner—Marc S. Zimmer
(74) Attorney, Agent, or Firm—James L. De Cesare

(57) ABSTRACT

A new composition of matter is a blend of (i) a crosslinked elastomeric silicone polyether and (ii) a crosslinked elastomeric silicone containing alkyl groups having 3–40 carbon atoms. The new composition can be used in preparing water-in-oil emulsions, and clear solutions containing an oil(s) or an oil-soluble active ingredient(s).

18 Claims, No Drawings

MIXTURES OF SILICONE ELASTOMERS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to a blend of certain silicone elastomers which can be used to compatibilize organic oils. The blend can also be used to prepare water-in-organic oil emulsions. The organic oils can be as polar as sunflower oil known to have an interfacial tension of about 19.3 mN/m. These benefits cannot be achieved using only one of the silicone elastomers.

For example, it was determined that Vitamin A was not soluble in either one of the silicone elastomers, but that it could be solubilized in a blend of the two silicone elastomers. This provides an improved delivery system for active ingredients such as Vitamin A, which are generally considered to be difficult to solubilize.

If desired, emulsions containing a blend of the silicone elastomers can be used for delivering water soluble active ingredients such as Vitamin C and α-hydroxy acids. In addition, it has been demonstrated that certain linear silicone polyethers can be used in place of one of the silicone elastomers in forming these new blends.

BACKGROUND OF THE INVENTION

A crosslinked elastomeric silicone polyether is disclosed in U.S. Pat. No. 5,811,487 (Sep. 22, 1998). A crosslinked elastomeric silicone containing alkyl groups having 3–40 carbon atoms is disclosed in U.S. Pat. No. 5,880,210 (Mar. 9, 1999). Both of these U.S. patents are assigned to the same assignee as the present invention.

However, neither of the common assignee's patents describe as a new composition of matter, a blend of (i) a crosslinked elastomeric silicone polyether, and (ii) a crosslinked elastomeric silicone containing alkyl groups having 3–40 carbon atoms.

The patents also fail to suggest either a water-in-oil emulsion containing the new composition of matter, or a clear solution containing the new composition of matter.

The patents further fail to suggest as a second new composition of matter, a blend of (i) a linear silicone polyether, and (ii) the crosslinked elastomeric silicone containing alkyl groups having 3–40 carbon atoms. In addition, the patents fail to suggest a water-in-oil emulsion containing the second new composition of matter.

These new and novel concepts are the subject matter of the present invention.

BRIEF SUMMARY OF THE INVENTION

This invention relates to a new composition of matter which is a blend of (i) a crosslinked elastomeric silicone polyether, and (ii) a crosslinked elastomeric silicone containing alkyl groups having 3–40 carbon atoms.

The invention also relates to a water-in-oil emulsion containing this composition of matter. In addition, the invention relates to a clear solution containing the composition.

In an alternate embodiment of the invention, a second new composition of matter is provided, and it is a blend of (i) a linear silicone polyether, and (ii) the crosslinked elastomeric silicone containing alkyl groups having 3–40 carbon atoms.

According to this alternate embodiment, a water-in-oil emulsion can also be formed containing the second new composition of matter.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

One composition of matter according to the present invention is a blend of (i) a crosslinked elastomeric silicone polyether, and (ii) a crosslinked elastomeric silicone containing alkyl groups having 3–40 carbon atoms.

The crosslinked elastomeric silicone polyether and methods of preparing crosslinked elastomeric silicone polyethers are described in detail in the common assignee's U.S. Pat. No. 5,811,487, incorporated herein by reference.

Generally, such crosslinked elastomeric silicone polyethers are prepared by reacting an ≡Si-H containing polysiloxane (A) and a mono-alkenyl polyether (B) in the presence of a platinum catalyst, until an ≡Si-H containing siloxane with polyether groups (C) is formed. The ≡Si-H containing siloxane with polyether groups (C) is then reacted with an unsaturated hydrocarbon (D) such as an alpha, omega-diene, in the presence of a solvent (E) and a platinum catalyst, until a silicone elastomer is formed by crosslinking and addition of ≡SiH across double bonds in the alpha, omega-diene (D).

The crosslinked elastomeric silicone containing alkyl groups having 3–40 carbon atoms and methods of preparing crosslinked elastomeric silicones containing alkyl groups having 3–40 carbon atoms are described in detail in the common assignee's U.S. Pa. No. 5,880,210, incorporated herein by reference.

Generally, such crosslinked elastomeric silicones containing alkyl groups having 3–40 carbon atoms are prepared by reacting an ≡Si-H containing polysiloxane (A), an alpha-olefin (B), and an alpha, omega-diene (C). The reaction is conducted in the presence of a platinum catalyst, and in the presence of a low molecular weight silicone oil or other solvent (D). The reaction is carried out by grafting long chain alkyl groups from the alpha-olefin (B) onto the ≡Si-H containing polysiloxane (A), and then crosslinking and addition of ≡Si-H in the grafted ≡Si-H containing polysiloxane across double bonds in the alpha, omega-diene (C).

While the crosslinked elastomeric silicone containing alkyl groups may contain alkyl groups having 3–40 carbon atoms, preferably, the crosslinked elastomeric silicone containing alkyl groups should contain alkyl groups having 16–30 carbon atoms.

In preparing blends according to the present invention, the crosslinked elastomeric silicone polyether and the crosslinked elastomeric silicone containing alkyl groups having 3–40 carbon atoms are mixed, i.e., blended, in a weight ratio of from 4:1 to 1:8, preferably 1:1 to 1:4.

Both the crosslinked elastomeric silicone polyether and the crosslinked elastomeric silicone containing alkyl groups having 3–40 carbon atoms constitute polymeric molecules which are crosslinked together to form a gel consisting of a three-dimensional molecular polymeric network containing tens, hundreds, and thousands of crosslinking units between and among the polymeric molecules. Typically, they each contain and are swollen with from 65 to 98 percent by weight of an oil.

Both U.S. Pat. No. 5,811,487 and U.S. Pat. No. 5,880,210 contain extensive lists of appropriate oils which can be used, among which are volatile polydimethylsiloxanes such as octamethyltrisiloxane and decamethylcyclopentasiloxane, nonvolatile polydimethylsiloxanes, aliphatic hydrocarbons such as pentane and heptane, aromatic hydrocarbons such as benzene and toluene, alcohols such as methanol and ethanol, aldehydes such as formaldehyde, ketones such as acetone and methyl ethyl ketone, amines such as methylamine, esters such as ethyl acetate, ethers such as tetrahydrofuran, glycols such as glycerol, glycol ethers such as ethylene glycol monomethylether, alkyl halides such as chloroform and carbon tetrachloride, aromatic halides such as chlorobenzene, flavoring agents such as peppermint oil, and fragrances such as musk and myrrh.

One particularly suitable use of the mixture of the crosslinked elastomeric silicone polyether and the crosslinked elastomeric silicone containing alkyl groups having 3–40 carbon, is for the preparation of water-in-oil emulsions consisting of an aqueous disperse phase and an oil continuous phase. In that application, the aqueous phase may contain a water soluble active ingredient, and the oil phase may contain an oil or an oil soluble active ingredient.

The water soluble active ingredient for the aqueous phase of the water-in-oil emulsion can be, for example, (i) a water soluble Vitamin, (ii) a water soluble drug, or (ii) an α-hydroxy acid such as glycolic acid, lactic acid, tartaric acid, and citric acid, i.e., fruit acids. In this latter instance, significant benefits can be realized as fruit acids have been alleged to be capable of diminishing fine skin lines and pigmentation spots, as well as stimulating collagen which allows the skin to repair itself.

The common assignee's U.S. Pat. No. 5,948,855 (Sep. 7, 1999), incorporated herein by reference, contains an extensive list of some appropriate water soluble Vitamins and water soluble drugs which can be used, among which are Vitamin C, Vitamin $B_1$, Vitamin $B_2$, Vitamin $B_6$, Vitamin $B_{12}$, niacin, folic acid, biotin, and pantothenic acid. The water-soluble vitamin can be used in the water-in-oil emulsion in amounts of from 0.01 to about 50 percent by weight.

The oil for the oil phase of the water-in-oil emulsion is most preferably an organic oil, generally, a natural oil that is derived from an animal, a vegetable, or a mineral source. Modern cosmetic oils are most representative of the organic oil, and among the more common organic oils known to be safe for cosmetic purposes are almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

The common assignee's U.S. Pat. No. 5,948,855 (Sep. 7, 1999), also contains an extensive list of some appropriate oil soluble active ingredients such as vitamins and drugs which can be used in the oil phase of the water-in-oil emulsion, among which are vitamins, including but not limited to, Vitamin $A_1$, RETINOL, $C_2$–$C_{18}$ esters of RETINOL, Vitamin E, TOCOPHEROL, esters of Vitamin E, and mixtures thereof. RETINOL includes trans-RETINOL, 13-cis-RETINOL, 11-cis-RETINOL, 9-cis-RETINOL, and 3,4-didehydro-RETINOL. Other vitamins which are appropriate include RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE. The oil-soluble vitamin or drug can be used in the water-in-oil emulsion in amounts of from 0.01 to about 50 percent by weight.

In preparing water-in-oil emulsions according to the present invention, the aqueous phase will generally comprise 0.1 to 99 percent by weight of the emulsion, including the weight of any water-soluble active ingredient. The oil phase will comprise 1 to 99.9 percent by weight of the emulsion, including the weight of the crosslinked elastomeric silicone polyether, the weight of the crosslinked elastomeric silicone containing alkyl groups having 3–40 carbon atoms, and the weight of the oil or oil-soluble active ingredient. Preferably, the aqueous phase comprises 20 to 95 percent by weight of the emulsion, and the oil phase comprises 5 to 80 percent by weight of the emulsion.

When clear solutions are desired rather than emulsions, the crosslinked elastomeric silicone polyether, the crosslinked elastomeric silicone containing alkyl groups having 3–40 carbon atoms, and the oil or oil-soluble active ingredient, are used in generally the same proportions as noted above. Clear solutions can be obtained by hand shaking the ingredients rather than by mixing them mechanically.

In some instances, it may be desirable to use a silicone polyether that is not a crosslinked elastomer. In a second embodiment of the present invention, therefore, a linear silicone polyether can be substituted for the crosslinked elastomeric silicone polyether. One such linear silicone polyether has a structure generally corresponding to the formula:

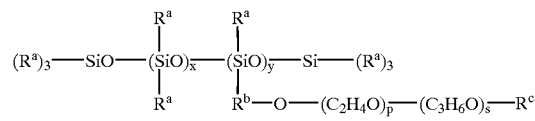

In the formula, $R^a$ is an alkyl group of one to six carbon atoms; $R^b$ is the radical —$C_mH_{2m}$—; $R^c$ is a terminating radical such as hydrogen, an alkyl group of one to six carbon atoms, or an aryl group such as phenyl. m has a value of two to eight. p and s each have a value such that the oxyalkylene segment —$(C_2H_4O)_p$—$(C_3H_6O)_s$— has a molecular weight in the range of 400 to 5,000. The oxyalkylene segment preferably contains 50–99 mole percent of oxyethylene units —$(C_2H_4O)_p$—, and 1–50 mole percent of oxypropylene units —$(C_3H_6O)_s$—. x has a value of 10 to 500. y has a value of 2 to 100.

Preferably, $R^a$ and terminating radical $R^c$ are both methyl groups. m is preferably three or four. The group $R^b$ is most preferably the —$(CH_2)_3$— group. The values of p and s are such as to provide a molecular weight of the oxyalkylene segment —$(C_2H_4O)_p$—$(C_3H_6O)_s$— of between about 1,000 to about 3,000. Most preferably, p should be 4 to 60, and s should be 0 to 60. These types of linear silicone polyethers are generally known in the art, and are commercially available from global sources such as the Dow Corning Corporation, Midland, Mich., USA.

EXAMPLES

The following examples are set forth in order to illustrate this invention in more detail.

Example 1—Water-in-oil Emulsion (W/O) Containing Sunflower Oil 10.0 gram of a crosslinked elastomeric silicone polyether prepared according to methods described in U.S. Pat. No. 5,811,487, in which about 20 percent of the repeating units in its backbone contained units that included the moiety —$(CH_2CH_2O)_n$— in which n had a value of 12, were weighed into a blender cup. To the blender cup were added 10.0 gram of a crosslinked elastomeric silicone containing alkyl groups having 16 carbon atoms prepared according to methods described in U.S. Pat. No. 5,880,210. These two ingredients were blended together using a mechanical mixer set at medium speed for about 30 seconds. 10.0 gram of this mixture were weighed into a glass beaker along with 20.0 gram of sunflower oil, and the contents of the beaker were mixed using a mechanical mixer set at a speed of 600 rpm (63 rad/s). After about 5 minutes of mixing, 70.0 gram of deionized water were added to the beaker over a 15 minute period using a peristaltic pump. The product obtained was a water-in-oil emulsion which had the consistency of a white cream.

Example 2—W/O Emulsion Containing Sunflower Oil & Mineral Oil 5.02 gram of the crosslinked elastomeric silicone polyether used in Example 1 were weighed into a glass beaker, along with 5.03 gram of the crosslinked elastomeric silicone containing alkyl groups having 16 carbon atoms used in Example 1, 10.21 gram of sunflower oil, and 10.04 gram of mineral oil. The four ingredients were mixed together using a mechanical mixer at 600 rpm (63 rad/s). After about 5 minutes of mixing, 76.78 gram of deionized water were added to the beaker over a 15 minute period while mixing at 800 rpm (84 rad/s). The mixing speed was increased to 1,000 rpm (105 rad/s) after the addition of water and continued for another 15 minutes. The product obtained was a water-in-oil emulsion which had the consistency of a white cream.

Example 3—W/O Emulsion Containing Sunflower Oil 10.0 gram of the crosslinked elastomeric silicone polyether used in Example 1 were weighed into a glass beaker, along with 20.2 gram of a crosslinked elastomeric silicone containing alkyl groups having 18 carbon atoms, and 10.30 gram of sunflower oil. The three ingredients were mixed together using a mechanical mixer at 600 rpm (63 rad/s). After about 5 minutes of mixing, 10.1 gram of deionized water were added to the beaker over a 15 minute period. The product obtained was a water-in-oil emulsion which had the consistency of a white cream.

Example 4—W/O Emulsion Containing Sunflower Oil 13.3 gram of the crosslinked elastomeric silicone containing alkyl groups having 16 carbon atoms used in Example 1 were weighed into a blender cup, along with 6.7 gram of a linear silicone polyether instead of a crosslinked elastomeric silicone polyether. The linear silicone polyether had a viscosity of about 1,700 centistoke ($mm^2/s$), and a structure generally corresponding to the formula shown previously, in which all of the $R^a$ groups were methyl and where p and s each had a value of about 18. These two ingredients were blended together at a medium setting using a mechanical mixer for about 30 seconds. The two silicone emulsifiers and 15.0 gram of sunflower oil were mixed together using the mechanical mixer at 600 rpm (63 rad/s). After about 5 minutes of mixing, 15.0 gram of deionized water were added to the beaker over a 15 minute period using a peristaltic pump. Upon completion of the addition of water, the ingredients were mixed for an additional 5 minutes. The product obtained was a water-in-oil emulsion which had the consistency of a white cream.

Example 5—Clear Solution Containing Vitamin A Palmitate 7.97 gram of the crosslinked elastomeric silicone polyether used in Example 1, and 2.22 gram of Vitamin A Palmitate, i.e., Retinyl Palmitate, were weighed into a glass beaker. Mixing these two ingredients by hand shake resulted in forming a turbid mixture in the beaker. 2.00 gram of the turbid mixture were weighed into another glass beaker, along with 2.00 gram of the crosslinked elastomeric silicone containing alkyl groups having 18 carbon atoms used in Example 3. The beaker contents were mixed together by simply hand shaking the beaker. This resulted in forming a clear solution in the beaker.

While the blends, the emulsions, and the clear solutions described herein are useful in applications requiring any benefit attributed to organosilicon materials, these blends, emulsions, and clear solutions are primarily intended for use in personal care. Thus, they can be used alone or combined with cosmetic ingredients to form a number of over-the-counter (OTC) personal care products. For example, they are useful as carriers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, and provide conditioning benefits.

In cosmetics, they can function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, they can impart a dry and silky-smooth feel.

These blends, emulsions, and clear solutions are also capable of functioning as carriers for pharmaceuticals, biocides, herbicides, pesticides, and other biologically active substances; and they have utility as additives for cellulosic or synthetic nonwoven carrier substrates used in wet-like cleansing wipes such as wet-wipes, tissues, and towels, marketed generally for personal hygiene and household cleaning tasks.

While elastomeric silicones prepared according to the common assignee's U.S. Pat. Nos. 5,811,487 and 5,880,210, are most preferred for use according to this invention, other types of elastomeric silicones may be employed herein without departing from the spirit of the invention, provided they are similar in performance and benefits to the preferred elastomeric silicones. For example, they can be prepared by using other kinds of organosilicon monomers as set forth in detail in U.S. Pat. No. 5,948,855. They can also be prepared by the one pot method as outlined in another of the common assignee's U.S. Pat. No. 5,889,108 (Mar. 30, 1999).

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition of matter comprising a blend of (i) a crosslinked elastomeric silicone polyether, and (ii) a crosslinked elastomeric silicone containing alkyl groups having 16 to 30 carbon atoms, the crosslinked elastomeric silicone polyether and the crosslinked elastomeric silicone containing alkyl groups having 3–40 carbon atoms being present in the blend in a weight ratio of 4:1 to 1:8.

2. A composition according to claim 1 in which the crosslinked elastomeric silicone (i) and the crosslinked elastomeric silicone (ii) contain and are swollen with from 65 to 98 percent by weight of an oil.

3. A composition according to claim 2 in which the crosslinked elastomeric silicone (i) and the crosslinked elastomeric silicone (ii) each comprise polymeric molecules crosslinked to form gels consisting of three-dimensional molecular polymeric networks containing tens, hundreds, and thousands of crosslinking units between and among polymeric molecules.

4. A water-in-oil emulsion comprising an aqueous disperse phase and an oil continuous phase, the oil phase containing the composition defined in claim 1.

5. A water-in-oil emulsion according to claim 4 in which one or both of the aqueous phase contains a water soluble active ingredient, or the oil phase contains an oil or an oil soluble active ingredient.

6. A water-in-oil emulsion according to claim 5 in which the water soluble active ingredient in the aqueous phase is selected from the group consisting of water soluble Vitamins, water soluble drugs, and α-hydroxy acids; and the oil or oil soluble active ingredient in the oil phase is selected from the group consisting of volatile polydimethylsiloxanes, nonvolatile polydimethylsiloxanes, aliphatic hydrocarbons, aromatic hydrocarbons, alcohols, aldehydes, ketones, amines, esters, ethers, glycols, glycol ethers, alkyl halides, aromatic halides, flavoring agents, fragrances, oil soluble Vitamins, oil soluble drugs, and natural oils derived from animal, vegetable, and mineral sources.

7. A water-in-oil emulsion according to claim 6 in which the aqueous phase comprises 0.1 to 99 percent by weight of the emulsion including the weight of the water-soluble active ingredient, and the oil phase comprises 1 to 99.9 percent by weight of the emulsion including the weight of the composition defined in claim 1 and the oil or oil-soluble active ingredient.

8. A water-in-oil emulsion according to claim 7 in which the aqueous phase comprises 20 to 95 percent by weight of the emulsion, and the oil phase comprises 5 to 80 percent by weight of the emulsion.

9. A clear solution comprising the composition defined in claim 1 and an oil or oil soluble active ingredient.

10. A composition of matter comprising a blend of (i) a linear silicone polyether, and (ii) a crosslinked elastomeric silicone containing alkyl groups having 3–40 carbon atoms, the linear silicone polyether (i) and the alpha, omega-diene crosslinked elastomeric silicone (ii) being present in the blend in a weight ratio of 4:1 to 1:8.

11. A composition according to claim 10 in which the linear silicone polyether (i) has the formula:

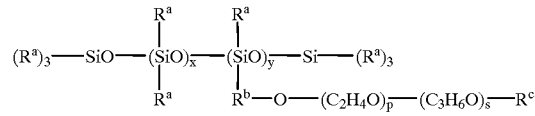

where $R^a$ is an alkyl group of one to six carbon atoms; $R^b$ is the radical —$C_mH_{2m}$—; $R^c$ is a terminating radical selected from the group consisting of hydrogen, an alkyl group of one to six carbon atoms, or an aryl group; m has a value of two to eight; p and s have values such that the oxyalkylene segment —$(C_2H_4O)_p$—$(C_3H_6O)_s$— has a molecular weight in the range of 400 to 5,000; the segment having 50–99 mole percent of oxyethylene units —$(C_2H_4O)_p$— and 1–50 mole percent of oxypropylene units —$(C_3H_6O)_s$—; x has a value of 10 to 500; and y has a value of 2 to 100.

12. A composition according to claim 10 in which the crosslinked elastomeric silicone (ii) contains and is swollen with from 65 to 98 percent by weight of an oil.

13. A composition according to claim 10 in which the crosslinked elastomeric silicone (ii) comprises polymeric molecules which are crosslinked together to form a gel consisting of a three-dimensional molecular polymeric network containing tens, hundreds, and thousands of crosslinking units between and among the polymeric molecules.

14. A water-in-oil emulsion comprising an aqueous disperse phase and an oil continuous phase, the oil phase containing the composition defined in claim 10.

15. A water-in-oil emulsion according to claim 14 in which one or both of the aqueous phase contains a water soluble active ingredient, or the oil phase contains an oil or an oil soluble active ingredient.

16. A water-in-oil emulsion according to claim 15 in which the water soluble active ingredient in the aqueous phase is selected from the group consisting of water soluble Vitamins, water soluble drugs, and α-hydroxy acids; and the oil or oil soluble active ingredient in the oil phase is selected from the group consisting of volatile polydimethylsiloxanes, nonvolatile polydimethylsiloxanes, aliphatic hydrocarbons, aromatic hydrocarbons, alcohols, aldehydes, ketones, amines, esters, ethers, glycols, glycol ethers, alkyl halides, aromatic halides, flavoring agents, fragrances, oil soluble Vitamins, oil soluble drugs, and natural oils derived from animal, vegetable, and mineral sources.

17. A water-in-oil emulsion according to claim 16 in which the aqueous phase comprises 0.1 to 99 percent by weight of the emulsion including the weight of the water-soluble active ingredient, and the oil phase comprises 1 to 99.9 percent by weight of the emulsion including the weight of the composition defined in claim 11 and the oil or oil-soluble active ingredient.

18. A water-in-oil emulsion according to claim 17 in which the aqueous phase comprises 20 to 95 percent by weight of the emulsion, and the oil phase comprises 5 to 80 percent by weight of the emulsion.

* * * * *